United States Patent
Ghalib et al.

(10) Patent No.: US 11,679,226 B2
(45) Date of Patent: Jun. 20, 2023

(54) METHODS AND SYSTEMS FOR DELIVERING GAS TO A PATIENT

(71) Applicant: Fisher & Paykel Healthcare Limited, Auckland (NZ)

(72) Inventors: Ali Ghalib Abdul Rahman Ghalib, Auckland (NZ); Lina Tessy, Auckland (NZ); Wisnu Arya Surendra, Auckland (NZ); Jessica Kristen Chan, Auckland (NZ); Joseph Patrick Walter Strevens, Auckland (NZ); Monika Baumann, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1409 days.

(21) Appl. No.: 15/303,728

(22) PCT Filed: Apr. 16, 2015

(86) PCT No.: PCT/NZ2015/050045
§ 371 (c)(1),
(2) Date: Oct. 12, 2016

(87) PCT Pub. No.: WO2015/160268
PCT Pub. Date: Oct. 22, 2015

(65) Prior Publication Data
US 2017/0028159 A1    Feb. 2, 2017

Related U.S. Application Data

(60) Provisional application No. 62/066,254, filed on Oct. 20, 2014, provisional application No. 61/980,442, filed on Apr. 16, 2014.

(51) Int. Cl.
*A61M 16/16* (2006.01)
*A61M 13/00* (2006.01)
(Continued)

(52) U.S. Cl.
CPC ............. *A61M 16/16* (2013.01); *A61B 17/34* (2013.01); *A61M 13/003* (2013.01);
(Continued)

(58) Field of Classification Search
CPC ............... A61M 16/16; A61M 16/022; A61M 16/0051; A61M 16/109; A61M 13/003;
(Continued)

(56) References Cited

U.S. PATENT DOCUMENTS 6,272,933 B1 * 8/2001 Gradon ............. A61M 16/1075
73/866.5
7,983,542 B2    7/2011 McGhin et al.
(Continued)

FOREIGN PATENT DOCUMENTS

CA    2789613 A1 *  3/2014 .......... A61M 13/003
EP    0885623 A2    12/1998
(Continued)

OTHER PUBLICATIONS

International Search Report; PCT/NZ2015/050045, dated Oct. 22, 2015; 8 pages.

*Primary Examiner* — Laura A Bouchelle
(74) *Attorney, Agent, or Firm* — Knobbe, Martens, Olson & Bear, LLP

(57) ABSTRACT

A system is provided for delivering gas to a patient during a medical procedure. The system comprises a heater arranged to heat at least one of the gas and a humidification liquid. The system comprises a controller arranged to control the system according to a first mode during delivery of a first flow rate of gas and a second mode during delivery of a second flow rate of gas. The controller monitors an electrical characteristic of the heater to select the mode of operation and/or to determine an operating state of the system.

25 Claims, 16 Drawing Sheets

(51) Int. Cl.
*A61M 16/10* (2006.01)
*A61M 16/00* (2006.01)
*A61B 17/34* (2006.01)

(52) U.S. Cl.
CPC ...... *A61M 16/0051* (2013.01); *A61M 16/022* (2017.08); *A61M 16/109* (2014.02); *A61M 2205/3317* (2013.01); *A61M 2205/3334* (2013.01); *A61M 2205/3368* (2013.01); *A61M 2205/3379* (2013.01); *A61M 2205/3386* (2013.01)

(58) Field of Classification Search
CPC .. A61M 2205/3386; A61M 2205/3317; A61M 2205/3368; A61M 2205/3379; A61M 2205/3334; A61M 16/1045; A61M 16/1075; A61M 2205/36; A61B 17/34
See application file for complete search history.

(56) References Cited

U.S. PATENT DOCUMENTS

| | | | |
|---|---|---|---|
| 8,616,202 B2 * | 12/2013 | Tatkov | A61M 16/026 128/203.14 |
| 2002/0078733 A1 | 6/2002 | Seakins et al. | |
| 2005/0107767 A1 | 5/2005 | Ott et al. | |
| 2009/0184832 A1 * | 7/2009 | Lloyd et al. | A61M 13/003 604/26 |
| 2011/0120462 A1 | 5/2011 | Tatkov et al. | |
| 2011/0162647 A1 * | 7/2011 | Huby | A61M 16/16 128/203.14 |
| 2013/0131580 A1 * | 5/2013 | Blackhurst | A61B 18/00 604/26 |
| 2013/0233318 A1 | 9/2013 | Graham et al. | |
| 2013/0245539 A1 * | 9/2013 | Ott | A61M 16/0051 604/24 |
| 2013/0249697 A1 | 9/2013 | Lloyd et al. | |
| 2014/0116433 A1 * | 5/2014 | Ghalib | A61M 16/026 128/203.14 |

FOREIGN PATENT DOCUMENTS

| | | |
|---|---|---|
| GB | 2338420 | 12/1999 |
| JP | 2010-088934 A | 4/2000 |
| JP | 2002-286677 A | 10/2002 |
| JP | 2003-010334 | 1/2003 |
| WO | WO 00/69511 | 11/2000 |
| WO | WO 01/13981 A1 | 3/2001 |
| WO | WO 02/32486 A1 | 4/2002 |
| WO | WO 2007/019628 A1 | 2/2007 |
| WO | WO 2009/145646 A1 | 12/2009 |
| WO | WO 2011/078701 A1 | 6/2011 |
| WO | WO 2011/136664 A9 | 11/2011 |
| WO | WO 2012/065999 A2 | 5/2012 |

* cited by examiner

METHODS AND SYSTEMS FOR DELIVERING GAS TO A PATIENT

FIELD OF THE DISCLOSURE

The disclosure relates to methods, systems, and apparatus for delivering humidified gas to a patient.

BACKGROUND

Various medical procedures require the provision of gas, typically carbon dioxide, to a patient during the medical procedure. For example, two general categories of medical procedures that often require providing gas to a patient include closed type medical procedures and open type medical procedures.

In closed type medical procedures, an insufflator is arranged to deliver gas to a body cavity of the patient to inflate the body cavity or to resist collapse of the body cavity during the medical procedure. Examples of such medical procedures include laparoscopy and endoscopy, although an insufflator may be used with any other type of medical procedure as required. Endoscopic procedures enable a medical practitioner to visualize a body cavity by inserting an endoscope or the like through a natural opening or small puncture to generate an image of the body cavity. In laparoscopy procedures, a medical practitioner typically inserts a surgical instrument through a natural opening or small puncture to perform a surgical procedure in the body cavity. In some cases an initial endoscopic procedure may be carried out to assess the body cavity, and then a subsequent laparoscopy carried out to operate on the body cavity. Such procedures are widely used, for example, on the peritoneal cavity, or during a thoracoscopy, colonoscopy, gastroscopy, or bronchoscopy.

In open type medical procedures, such as open surgeries, gas is used to fill a surgical cavity, with excess gas spilling outward from the opening. The gas may also be used to provide a layer of gas over exposed internal body parts where there is no discernible cavity. For these procedures, rather than serving to inflate a cavity, the gas can be used to prevent or reduce desiccation and infection by covering exposed internal body parts with a layer of heated, humidified, sterile gas.

An system for delivering gas during these medical procedures can comprise an adjustable throttling pressure regulator and a gas flow controller. The system typically comprises, or is connected to, a source of gas that may be a remote source of pressurized gas, a gas canister, or the like, and is operative to control the pressure and/or flow of the gas from the gas source to a level suitable for delivery into the body cavity, usually via a cannula or needle inserted into the body cavity, or via a diffuser arranged to diffuse gas over and into the wound or surgical cavity.

The internal body temperature is typically around 37° C., and it can be desirable to closely match the temperature of the gas delivered from the system to normal body temperature. Likewise, the gas provided by the source of gas may be relatively dry, which can cause damage to the body cavity, including cell death and/or adhesions, so it can be desirable to increase the humidity level of the gas. A humidifier may therefore be located in the gas flow path to heat and humidify the gas before it enters the body cavity.

U.S. Pat. No. 8,206,337 of Fisher & Paykel Healthcare Limited, incorporated herein by reference in its entirety, discloses a system including an insufflator arranged to be connected to a remote source of pressurized gas, as may be provided via a gas supply system in a hospital, for example. The insufflator delivers gas, via tubing, to a humidifier that comprises a receptacle of liquid and a heater to heat the liquid to generate vapor. The humidified gas is delivered to a patient via further tubing that may also be heated. In one example, the insufflator and humidifier are located in separate housings connected together via suitable tubing and/or electrical connections. In another example, the insufflator and humidifier are located in a common housing arranged to be connected to a remote gas supply via suitable tubing.

Moreover, the same system can be used to provide respiratory assistance by delivering heated and/or humidified breathing gas to a patient, usually via a gas delivery conduit connected to a patient interface. The patient interface can comprise, for example, a face mask or a nasal cannula or the like. Such a system typically comprises, or is arranged to be connected to, a humidifier that humidifies the gas prior to delivery to the patient.

SUMMARY

Although the same equipment, including for example an insufflator and a humidifier, can be used for closed type medical procedures, open type medical procedures, and respiratory assistance, the operation of this equipment for each type of use can vary greatly. The present disclosure provides systems and methods for controlling a gas supply and humidification system in order to automatically determine which type of use the system is being used for and to adjust its operation in order to meet the different requirements of each type of use. This operates to prevent user error or inadvertent harm to the patient.

For example, when a gas supply and humidification system is used for an open type surgical procedure, a relatively high flow rate of gas is required, with a corresponding relatively high volume of liquid consumed to maintain the desired moisture content to sufficiently humidify the gas.

When used for a closed type surgical procedure, a lower flow rate of gas and/or a more intermittent supply of gas, and corresponding lower volume of liquid, are required.

In order for a gas supply and humidification system to be able to control the gas flow rate and humidity appropriate to each type of procedure or use, external sensing probes, typically a temperature probe and a flow probe, can be used. The outputs of these probes can be used by the gas supply system to control the gas flow rate and humidity to match the type of medical procedure or use. However, it can be expensive to provide such probes as well as difficult for medical staff to correctly connect the probes for proper operation. External probes also reduce the overall usability of the system and add extra external components that can be lost or broken and that need to be sterilized between uses.

Moreover, other conditions can occur that can significantly affect the operation of a gas supply and humidification system. For example, if the gas flow is limited or stopped, this can create a number of problems for the rest of the system. For example, this can happen in a system that is supplied with a discrete source of gas such as a gas bottle or canister that runs out. Also, the system can be significantly affected if a humidifier associated with the system runs out of liquid, for example, if the humidifying liquid has all evaporated.

The present disclosure provides control methods and systems for delivering gas to a patient that overcome or at least ameliorate one or more of these disadvantages.

In an embodiment, a system is described for delivering gas to a patient during a medical procedure. The system comprises, or is arranged to be provided with, a heater configured to heat at least one of the gas and a humidification liquid contained in a humidification chamber. The system is operative according to a first mode in which the medical procedure is a first medical procedure wherein the system delivers a first flow rate of gas and is operative according to a second mode in which the medical procedure is a second medical procedure wherein the system delivers a second, different, flow rate of gas. The system is configured to monitor an electrical characteristic of the heater and subsequently select the first mode or the second mode in response to the monitored electrical characteristic.

The first medical procedure may be an open medical procedure during which, in the first mode, the system delivers a relatively high flow rate of gas.

The second medical procedure may be a closed medical procedure during which, in the second mode, the system delivers a relatively low flow rate of gas and/or an intermittent flow of gas.

The flow rate of gas in one or each mode may be a constant flow of gas, a varying flow of gas, or an intermittent flow of gas. The desired flow rate of gas may be achieved by controlling a blower or pump, and/or by controlling a control valve and/or regulator.

The monitored electrical characteristic may be the power drawn by the heater. For example, the monitored electrical characteristic may be the power duty cycle of the heater. The power duty cycle, for example, can be calculated as the proportion of time during which the heater is drawing power. In an embodiment, the monitored characteristic may be the current drawn by the heater.

The electrical characteristic of the heater may be monitored for a predetermined time period, and an average of the electrical characteristic of the heater calculated for that time period. In an embodiment, the system can determine a mode of operation by comparing the calculated average of the electrical characteristic of the heater to a predetermined threshold.

In an embodiment, in an initial step, the heater is switched on and allowed to warm up during a warm-up period. For example, the heater may be switched on and allowed to warm up before the electrical characteristic of the heater is monitored.

In an embodiment, a method of controlling components of a gas supply and humidification system is described. The method comprises monitoring the power duty cycle of the heater and subsequently determining a shortage of humidification liquid in the humidification chamber by analyzing the monitored power duty cycle of the heater.

The power duty cycle and/or current draw of the heater may be monitored for a predetermined period of time and one or more averages calculated over the predetermined period of time. The average(s) are used to determine a shortage of humidification liquid in the humidification chamber.

A short term average power duty cycle and/or current draw of the heater may be calculated over a first predetermined period of time, and a long term average power duty cycle and/or current draw of the heater may be calculated over a longer predetermined period of time. For example, in an embodiment, the long term average is calculated over a time window that is two to ten times longer than the window for the short term average. Of course, other relative differences in the window size can be used. The difference between the long and short term averages can be used to determine a shortage of humidification liquid in the humidification chamber. In an embodiment, if the long term average is greater than the short term average by at least a first positive threshold amount, it is determined that the level of humidification liquid in the humidification chamber is low.

The difference between the long and short term averages of the power duty cycle and/or current draw of the heater may alternatively or additionally be used to determine that humidification liquid has been added to the humidification chamber. In an embodiment, if the short term average is greater than the long term average by at least a second positive threshold amount, it is determined that humidification liquid has been added to the humidification chamber.

If it is determined that humidification liquid has been added to the humidification chamber, further monitoring of the power duty cycle and/or current of the heater can be delayed until a stabilization time period has elapsed. This allows the system to stabilize.

The system can activate an indicator if it is determined that humidification liquid is low in the humidification chamber.

In an embodiment, the system can determine if the level of humidification liquid in the humidification chamber is low or empty at the start of the procedure, prior to monitoring the heater power duty cycle. This can be done by comparing at least one characteristic of the humidification system with at least one predetermined characteristic of a humidification system in which a predetermined sufficient amount of humidification liquid is present in the humidification chamber. The compared characteristic may, for example, be the output of a temperature sensor associated with the heater. In another embodiment, the compared characteristic is the heater power duty cycle.

In an embodiment, prior to entering normal operational mode, the system detects if gas is flowing through the system.

In an embodiment, a humidifier is described that provides humidified gas to a patient. The humidifier can comprise a humidification chamber and a heater to heat the humidification liquid in the humidification chamber to generate vapor to humidify gas delivered to the patient. The humidifier comprises a controller arranged to monitor the power duty cycle of the heater, that is, the proportion of time during which the heater is drawing power, and arranged to subsequently determine absence or shortage of humidification liquid in the humidification chamber in response to the monitored power duty cycle of the heater.

In an embodiment, an electrical characteristic of the heater is monitored. A determination is made as to whether gas is flowing through the system based on the monitored electrical characteristic. In an embodiment, the electrical characteristic may be the current drawn by the heater. In an embodiment, the electrical characteristic is the heater power duty cycle. The electrical characteristic may be monitored for a predetermined period of time, and an average of the electrical characteristic calculated over the predetermined period of time. The average of the electrical characteristic can be used to determine whether or not gas is flowing through the system.

In an embodiment, a short term average of the electrical characteristic is calculated over a first predetermined period of time, and a long term average of the electrical characteristic is calculated over a second, longer predetermined period of time. The difference between the long and short term averages of the electrical characteristic can be used to determine whether or not gas is flowing.

If the long term average of the electrical characteristic is greater than the short term average by at least a first positive threshold amount, it is determined that the gas flow rate has dropped below a normal operating range. The system can activate an indicator if it is determined that the gas flow rate has dropped.

If the short term average is greater than the long term average by at least a second positive threshold amount, it is determined that the flow rate of gas has increased.

In an embodiment, a calibration can be performed where the electrical characteristic of the heater is monitored and a calibration average of the electrical characteristic is calculated over a predetermined period of time. The calibration average of the electrical characteristic can be used as a reference to allow for varying electrical resistances of the heater.

In an embodiment, the heater is switched on and allowed to warm up prior to the electrical characteristic of the heater being monitored. The warm-up process can occur over a predetermined period of time at a calculated rate in order to avoid condensation buildup in the system.

In an embodiment, prior to monitoring the electrical characteristic of the heater, the system determines if a gas supply has been provided. If no gas supply is detected, the system can activate an indicator.

Further objects of the disclosed methods, systems, and apparatus will become apparent from the following description.

BRIEF DESCRIPTION OF THE DRAWINGS

A number of embodiments of the disclosed methods, systems, and apparatus will now be described by way of example with reference to the following drawings.

FIGS. 12, 12-1 and 12-2 are flow diagrams of an example embodiment of a method of controlling a medical gas delivery system in open mode.

DETAILED DESCRIPTION

Figure 1:
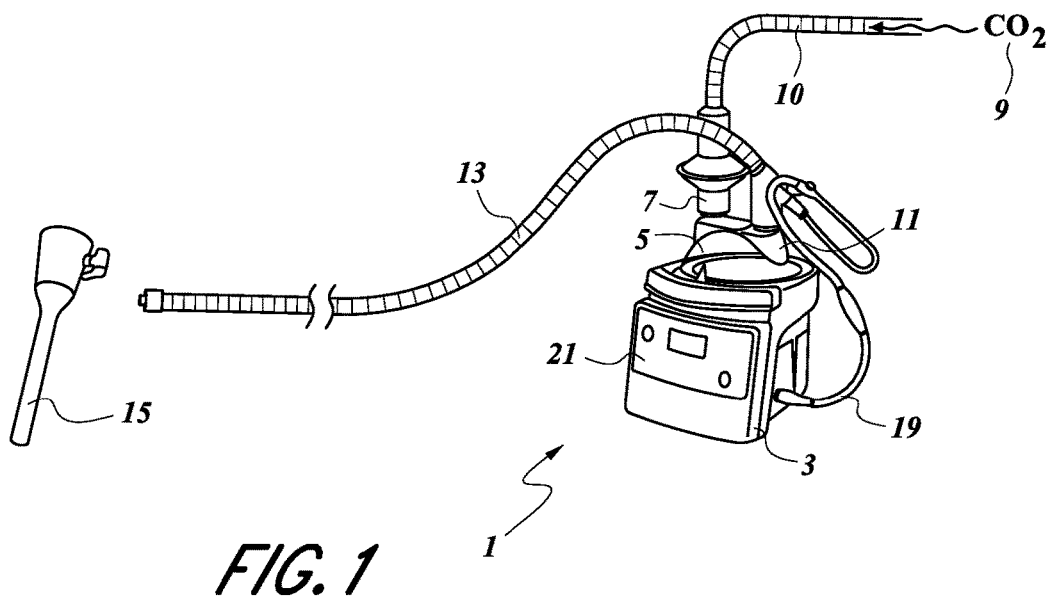
FIGS. 1-2 are schematic views of example embodiments of a medical gas delivery system.
Figure 2:
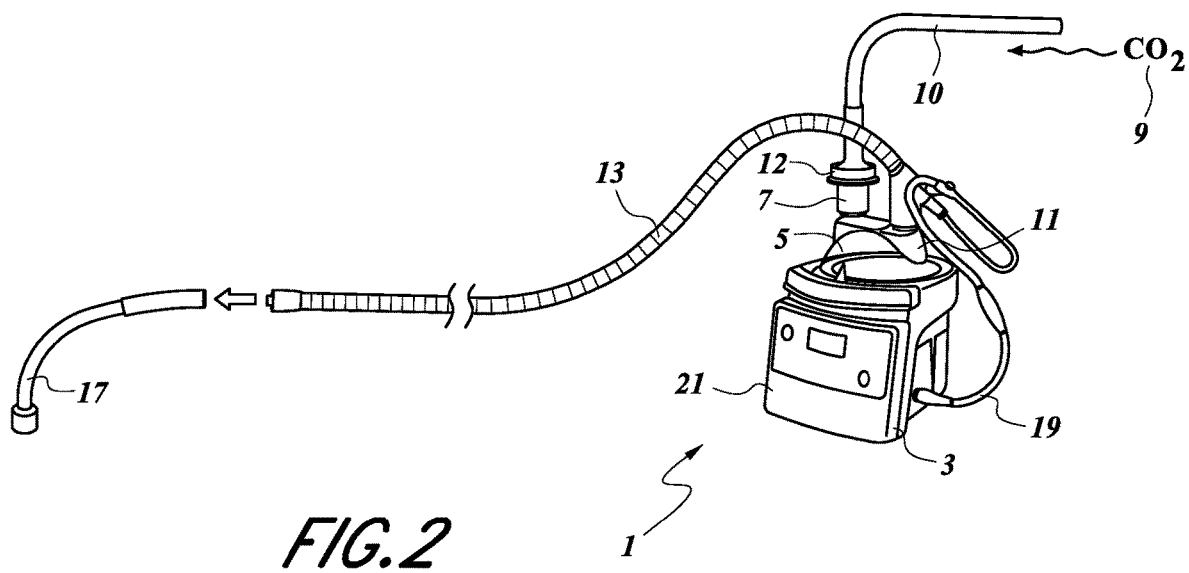

FIGS. 1 and 2 are schematic views of example embodiments of a humidification and gas delivery apparatus 1. The apparatus 1 comprises a base unit 3 and a humidification chamber 5 removably mounted on the base unit 3. The humidification chamber 5 comprises a gas inlet 7 arranged to be connected to a gas source 9 via an inlet conduit 10 to deliver the gas, for example carbon dioxide, into the chamber 5. The chamber 5 further comprises a gas outlet 11 arranged to be connected to a gas delivery conduit 13 to deliver humidified gas to a patient. A filter 12 (shown in FIG. 2) may be provided between the gas source 9 and the chamber 5 to filter the incoming gas.

In the embodiment of FIG. 1, an end of the gas delivery conduit 13 comprises a trocar 15 arranged to be connected to a patient for use in closed medical procedures such as endoscopy and laparoscopy. In the embodiment of FIG. 2, an end of the gas delivery conduit 13 comprises a diffuser 17 arranged to diffuse the humidified gas into a wound of a patient during open medical procedures, such as open surgery.

The apparatus 1 comprises, for example, a heater. The heater can comprise a heater plate on the base unit 3, for example. The heater is configured to heat humidification liquid in the chamber 5 to generate vapor. The humidification liquid is typically, but not necessarily, water. Gas from the gas source 9 flows into the chamber 5 and passes over the heated humidification liquid, thus taking up vapor and increasing in humidity level prior to delivery to the patient via the gas delivery conduit 13. The chamber 5 may alternatively or additionally comprise an integral heater or a heater located inside the chamber 5.

The gas delivery conduit 13 can also comprise or be provided with a heater. A heater for the gas delivery conduit 13 can ensure that the gas temperature is maintained at a desired level along the conduit 13 as well as minimize or eliminate the formation of condensation. A heater for the gas delivery conduit 13 can have a resistance wire provided in or attached to the conduit 13, or a wire or other heater element provided inside the conduit 13. A heater for the gas delivery conduit 13 may be electronically connected to the base unit 3 or to the chamber 5, for example by an electrical cable 19 to power the heater. Additionally or alternatively, the conduit 13 may be thermally insulated.

The apparatus 1 comprises a controller 21 arranged to control the apparatus 1, and in particular to control the flow rate, temperature, and humidity of gas delivered to the patient to be appropriate for the type of medical procedure for which the apparatus is being used. The controller 21 therefore controls, among other things, a heater for the humidification chamber 5 and/or a heater for the gas delivery conduit 13, if provided. The controller 21 can also control a regulator that regulates the flow rate of gas through the apparatus 1. The regulator may comprise a flow inducer and/or inhibiter such as a motorized fan. Valves and/or vents may additionally or alternatively be used to control flow rate. The controller 21 may comprise an electronic controller, that may be microprocessor-based, for example. The system can comprise memory and any electronic components capable of performing calculations as would be understood by those of skill in the art.

Figure 3:
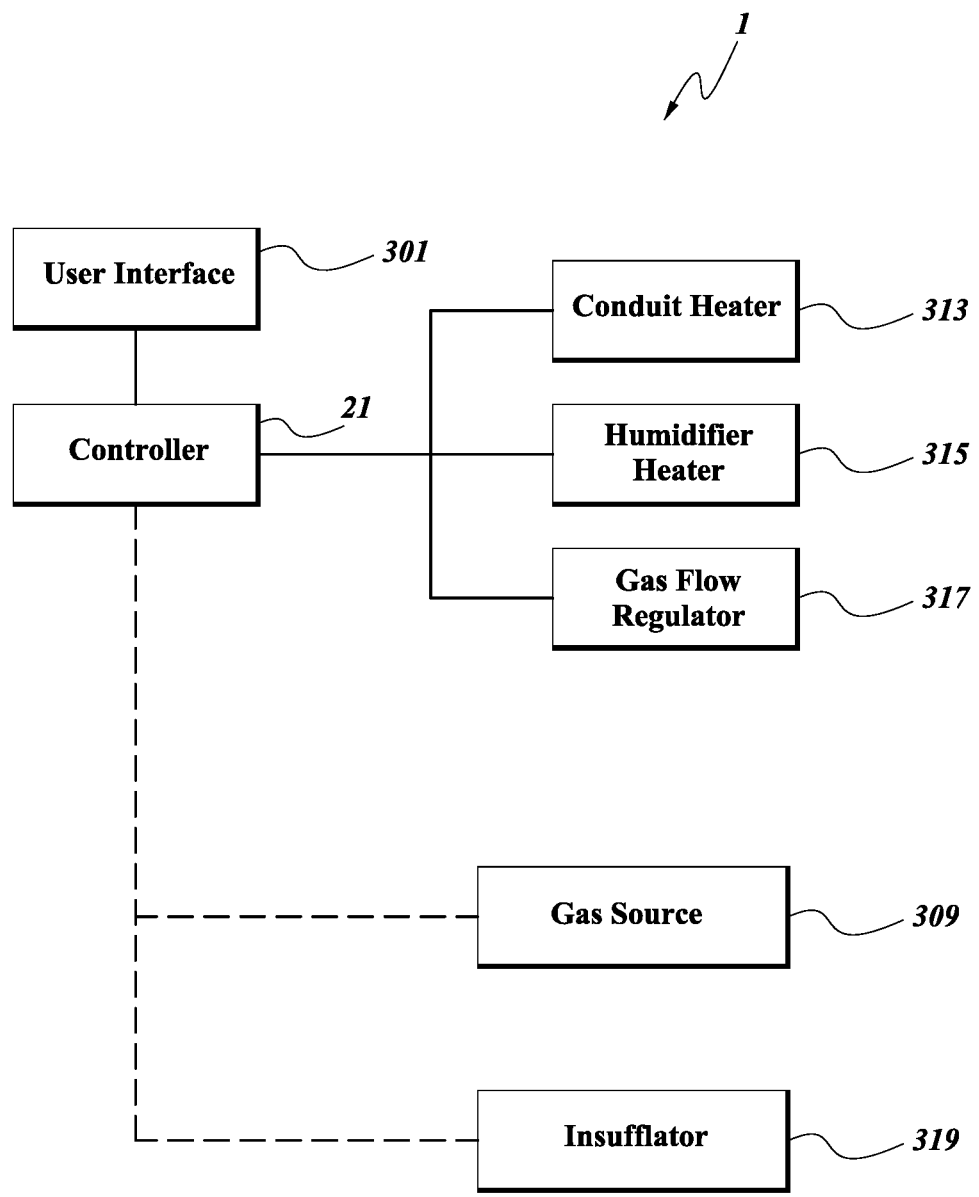
FIG. 3 is a schematic diagram of an example embodiment of a medical gas delivery system.

FIG. 3 a schematic diagram of an embodiment of the apparatus 1. The apparatus 1 can comprise, for example, a user interface 301, the controller 21, a conduit heater 313, a chamber heater 315, and a gas flow regulator 317. The user interface 301 can be used to operate the controller 21. The controller 21 provides electrical control signals to the conduit heater 313, the chamber heater 315, and, in some embodiments, the gas flow regulator 317, to control operations of those devices as described elsewhere herein. The controller 21 may also control a gas source 309 and/or an insufflator 319. In some embodiments, an insufflator controls the flow and the apparatus 1 reacts to that flow. In some embodiments, a gas bottle may provide a flow that can be controlled by a gas flow regulator or valving system.

The apparatus 1 is controlled to be operative in at least two modes.

In a first mode, for example, for use in open medical procedures such as open surgery, the controller 21 is configured to control the gas flow rate through the apparatus 1 to be relatively high. Consequently, the controller 21 controls the apparatus 1 to generate a relatively large volume of vapor to ensure the relatively high volume flow rate of gas is sufficiently humidified.

In a second mode, for example, for use in closed medical procedures such as endoscopic or laparoscopic procedures, the controller 21 is arranged to control the gas flow rate through the apparatus 1 to be relatively low. Consequently, the controller 21 controls the apparatus 1 to generate a relatively small volume of vapor to ensure the relatively low volume flow rate of gas is not excessively humidified.

The controller 21 is configured to at least (1) monitor one or more electrical characteristics of the one or more heaters in use, (2) generate outputs that are used to control the mode of operation of the apparatus 1, (3) detect gas flow through the apparatus 1, and/or (4) detect a water-out condition in the humidification chamber 5. A water-out condition occurs when there is an absence or shortage of humidification liquid in the humidification chamber 5.

In an embodiment, the controller 21 is arranged to monitor an electrical characteristic of the one or more heaters, such as the drawn power, the drawn current, or the power duty cycle, to determine the type of medical procedure for which the apparatus 1 is being used, and to subsequently control the apparatus 1 according to the first or second modes.

In an embodiment, the controller 21 is configured to monitor an electrical characteristic of the one or more heaters, such as the drawn power, the drawn current, the resistance, or the power duty cycle. One or more of these electrical characteristics are used to determine the flow or absence of flow of gas through the apparatus 1 and to subsequently activate an indicator of the gas flow rate being low or zero.

In an embodiment, the controller 21 is configured to monitor an electrical characteristic of the one or more heaters, such as the drawn power, the drawn current, or the power duty cycle, to determine an absence or shortage of humidification liquid in the chamber 5. If it is detected that the humidification liquid is low or absent, the controller 21 activates an indicator of a low or absent humidification liquid level. In an embodiment, under such a condition, the controller 21 can deactivate at least a portion of the apparatus 1. For example, the controller 21 can deactivate the chamber heater 315, the conduit heater 313, and/or the flow inducer or regulator 317.

The apparatus 1, as described above, may be used in a first mode suitable for open medical procedures such as open surgery. In the first mode, the flow rate of gas supplied to the patient is relatively high, and in one example, may be a substantially constant flow rate of around 10 L/min. The flow rate may be adjustable, either automatically or manually. A constant flow rate may be automatically or manually determined. The constant flow rate may be set according to the requirements of the particular patient. The flow rate may be controlled to ramp up from a lower initial level before reaching the desired constant level.

The apparatus 1 may also be used in a second mode, suitable for closed medical procedures, such as endoscopy or laparoscopy. In the second mode, a lower flow rate of gas is usually supplied to the patient, and in one example, may be supplied as a relatively low, pulsing flow rate rather than a constant low flow rate. Further, there may be periods when very low or no flow is supplied.

In each mode, the humidity of the gas supplied is controlled, and may be controlled to reach a minimum threshold. In one example, this minimum threshold is around 30 mg of humidifying liquid per liter of gas.

Prior to entering either mode, the controller may control the apparatus 1 according to a warm-up procedure that is arranged to pre-heat one or more heaters of the apparatus 1 for a given time period.

For the purposes of the following description, references to the heater are meant to refer to the chamber heater 315 (as shown in FIG. 3). However, it is to be noted that the heater can alternatively or additionally refer to the conduit heater 313, if provided.

Figure 4:
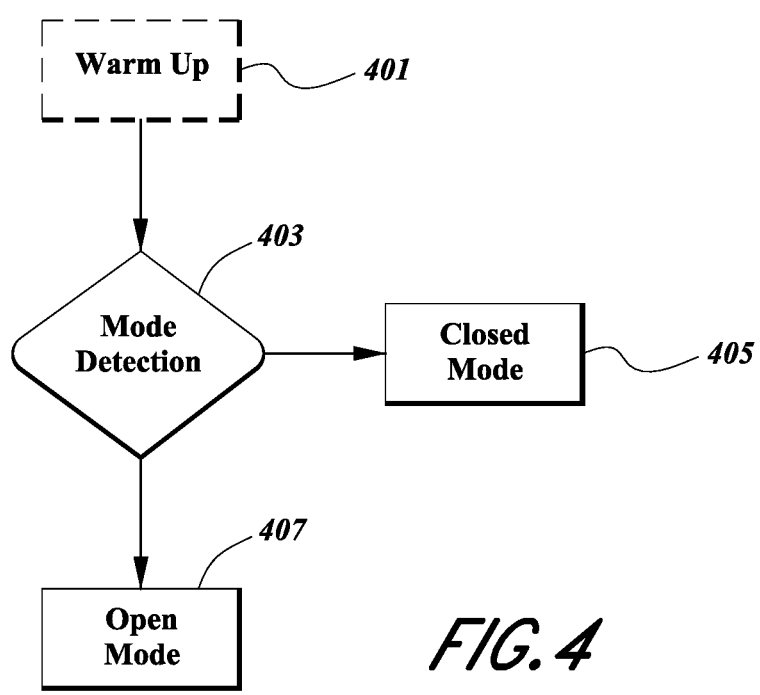
FIG. 4 is a flow diagram of an example embodiment of a method of controlling a medical gas delivery system.

FIG. 4 is a flow diagram of an embodiment of a method used by the controller 21 to determine a mode of operation. The system is powered up and allowed to warm up in a warm-up process 401. The warm-up process 401 comprises, for example, providing power to the heater until it reachs a predetermined threshold temperature. After the warm-up process 401, the system moves to a mode detection process 403. The mode detection process 403 determines the type of medical procedure for which the apparatus 1 is being used. The mode detection process 403 may be used as part of, or to initiate, subsequent control processes, including, for example, a closed mode process 405 and an open mode process 407.

Figure 5:
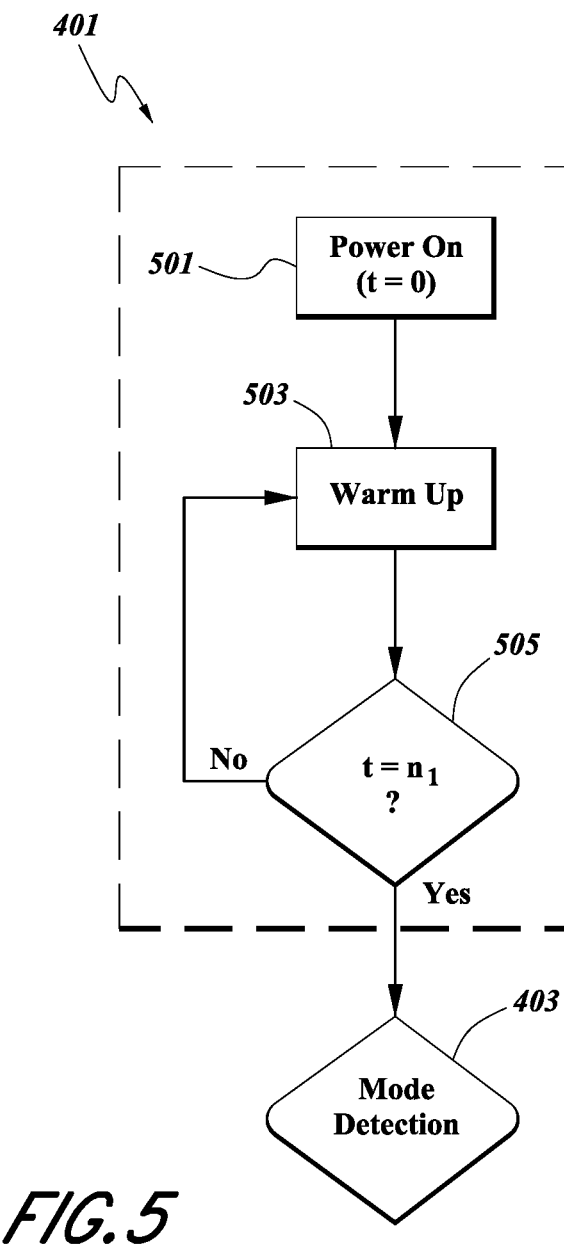
FIGS. 5-10 illustrate further details of the flow diagram of FIG. 4.

The warm-up process 401 is illustrated in greater detail in FIG. 5. The system powers on at 501. The heater is provided with power during the warm-up process at 503. The system then determines if a sufficient warm-up period has elapsed at 505. If it has not, then the system continues the warm-up process at 503. If a predetermined warm-up time period $n_1$ has elapsed, then the process moves on to the mode detection process 403.

The mode detection process 403 determines the type of medical procedure for which the apparatus 1 is being used. The gas flow requirements for an open medical procedure such as open surgery are relatively high, and the temperature of the humidification chamber heater and/or the gas delivery conduit heater temperature therefore also needs to be higher to maintain the desired humidity level of the relatively high gas flow. One or more heaters can be controlled to be at a set point temperature, sufficient to supply gas at the required humidity level. A temperature sensor or sensors can be provided to measure the temperature of one or more of the heaters. This measurement is used by the controller 21 to maintain the desired set point temperature.

Figure 6:
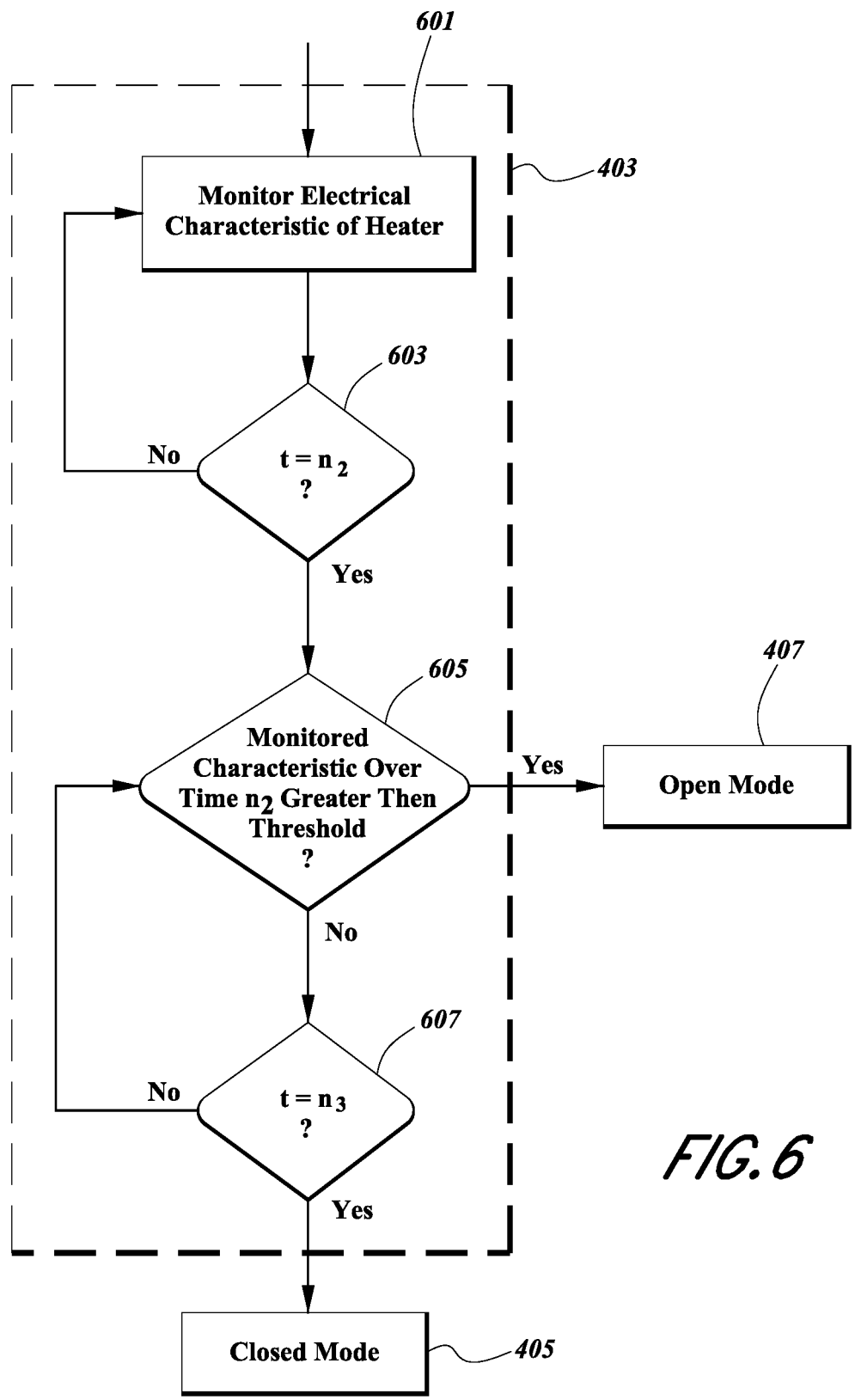

The mode detection process 403, as illustrated in more detail in FIG. 6, determines whether an open medical procedure such as open surgery is being performed by monitoring an electrical characteristic of the heater, such as the power drawn by the heater. A relatively high gas flow rate, such as that used during an open medical procedure, requires more power for the heater than a lower gas flow rate, such as that used during a closed medical procedure.

In an embodiment, the mode detection process 403 monitors one or more electrical characteristics of the heater at 601, such as, for example, the power duty cycle of the heater, i.e., the proportion of time during which the heater is drawing power. The one or more electrical characteristics is monitored for a predetermined time period $n_2$, as determined at 603. In an embodiment, the one or more electrical characteristics is averaged for that time period. The one or more electrical characteristics, or averaged one or more electrical characteristics, for the time period $n_2$ is then compared to a specific threshold at 605. If the one or more electrical characteristics, or averaged one or more electrical characteristics, exceeds the threshold, the controller 21 determines that the apparatus 1 is being used in an open medical procedure such as open surgery and controls the apparatus 1 according to the open mode process 407.

If the one or more electrical characteristics, or averaged one or more electrical characteristics, is below the threshold, the mode detection process 403 continues monitoring the one or more electrical characteristics for an extended time period $n_3$, as determined at 607. After the extended time period $n_3$, the one or more electrical characteristics, or averaged one or more electrical characteristics, is again compared to the threshold and if it is still below the threshold, the controller 21 controls the apparatus 1 according to the closed mode process 405. In the closed mode process 405, the flow of gas may be controlled at a relatively low constant flow rate or an intermittent or pulsing flow rate.

Figure 7:
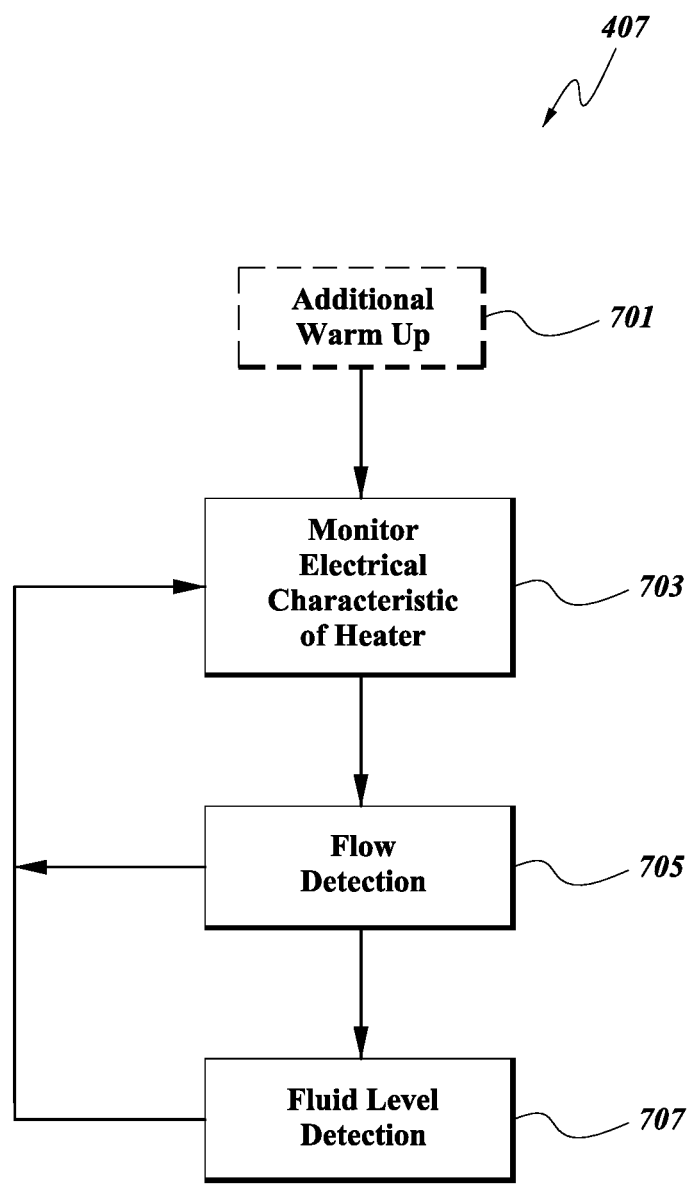
Figure 8:
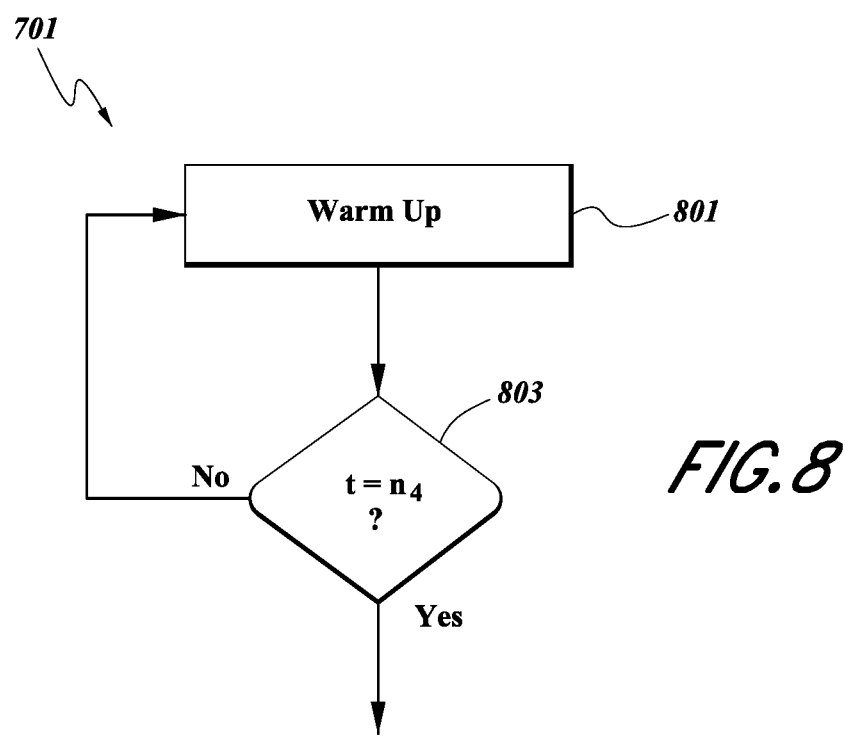

FIG. 7 illustrates an embodiment of the open mode process 407. The open mode process 407 can comprise an additional warm-up process 701. The additional warm-up process 701, as illustrated in FIG. 8, comprises applying additional power to the heater at 801 for a predetermined period of time $n_4$ until the additional warm-up period has expired.

Once the additional warm-up process 701 is finished, the system continues to monitor the one or more electrical characteristics at 703 for a predetermined period of time. In an embodiment, the predetermined period of time is 40 minutes. The one or more electrical characteristics at 703 can comprise, for example, the duty cycle and/or the current drawn by the heater. The system then performs a flow detection process 705 and/or a liquid level detection process 707 as described in further detail herein.

The voltage supplied to the heater is fixed by the power source of the apparatus 1, and therefore the current drawn by the heater will vary depending on how much heat the heater needs to generate to maintain the heater temperature at the set point temperature determined by the controller 21. The heater temperature is measured by the heater temperature sensor.

In an embodiment, the flow detection process 705 and the liquid level detection process 707 are only performed as part of the open mode process 407. However, the flow detection process 705 and/or the liquid level detection process 707 may also or alternatively be performed as part of the closed mode process 405.

In an embodiment, flow sensors and/or temperature sensors can be incorporated into any component of the apparatus 1 to provide additional data. For example, a temperature sensor can be used to determine the temperature of the humidification liquid in the humidification chamber 5.

In an embodiment, the power or current drawn by the heater can be used to determine and/or monitor ambient conditions and to calibrate the apparatus 1.

Figure 9:
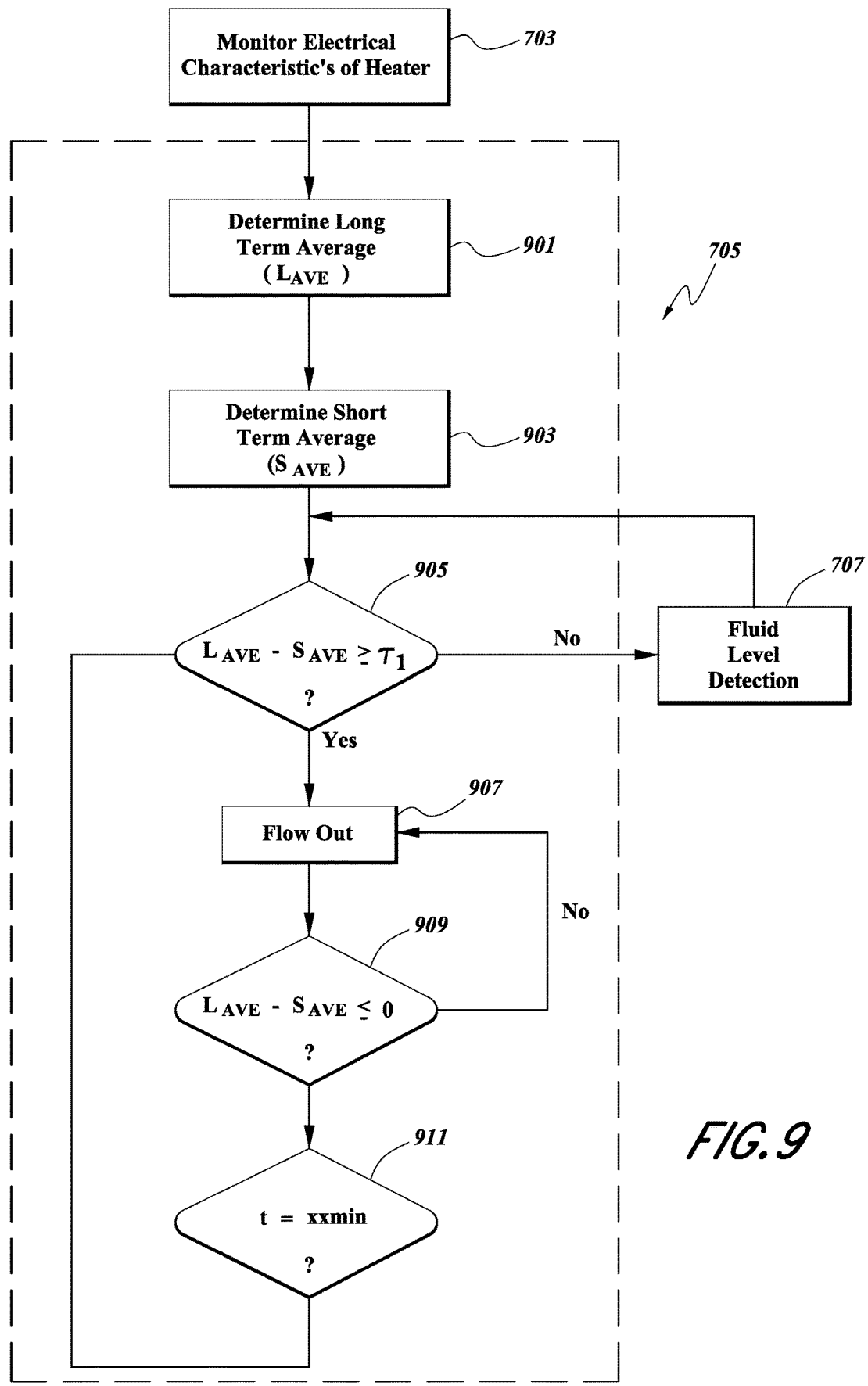

FIG. 9 illustrates additional details of the flow detection process 705. In an embodiment, electrical characteristics of the heater, such as the power duty cycle and the drawn current, are continuously averaged over two different time periods. The time periods include a short time period and a long time period. A long term average $L_{AVE}$ is determined at 901, and a short term average $S_{AVE}$ for the same electrical characteristic is determined at 903. Long and short term averages can be determined for all of the one or more electrical characteristics, including, for example, the heater power duty cycle and drawn current. Thus, for each electrical characteristic of the heater, the controller 21 calculates a short term average and a long term average. In an embodiment, these characteristics can be monitored during the warm-up procedure 701 and/or after the warm-up procedure 701 is complete.

In an embodiment, the flow detection process 705 is activated after the warm-up procedure 701 is complete (as shown in FIG. 7), that is, after the heater power duty cycle and drawn current have been averaged for the predetermined time period. Alternatively, as described above, the heater power duty cycle and drawn current can be averaged for a predetermined time period after the warm-up process is completed, as part of the flow detection process 705.

The flow detection process 705 determines if gas is flowing by comparing the difference between the long and short term averages of the drawn heater current to a threshold value. Although the described embodiment comprises one particular type of difference comparison, i.e., subtracting the short term average from the long term average and comparing the result to a threshold value, other types of difference comparisons can also be used; for example, the long term average could be subtracted from the short term average and compared to the negative of the threshold value. When using a different type of measurement to compare similar data, a person of skill in the art will understand that the decision steps in the described embodiment will be altered accordingly. Thus, the present embodiment, and all embodiments described herein, are provided by way of example and are not intended to be limiting.

If the difference at 905 is not greater than or equal to a threshold $\tau_1$, then the flow detection process 705 moves on to the liquid level detection process 707. If the difference is greater than or equal to the threshold $\tau_1$ at 905, then the flow detection process 705 determines that there is low or no gas flow at 907 and may activate a low gas flow indicator. This is because it is undesirable for the gas flow to be too low or to stop as this may adversely affect the medical procedure being carried out and may cause excess humidity to be produced. Excess humidity may compromise visual clarity in a body cavity for a medical practitioner.

If the difference between the long and short term averages calculated at 905 is close to zero, this is indicative of the gas flow being constant. However, if the difference is not close to zero, this can be indicative of the gas flow either having decreased and/or stopped, or having increased, depending on whether the difference is positive or negative. The flow detection process 705 is further operative to determine if gas flow is increasing, for example, when the apparatus 1 is initially connected to a source of gas or is connected to a new or replacement source of gas. The determination again determines the difference between the calculated long and short term averages of the drawn heater current at 909. If the difference (calculated by subtracting the short term average from the long term average) is negative, that is, less than zero, the flow detection process 705 determines that gas flow has been added and adjusts the apparatus 1 settings accordingly. The system then waits a predetermined period of time for the apparatus 1 settings to take effect and then returns to monitoring the long and short term averages at 905. If the difference is not negative, then the process returns to monitoring the flow out at 907.

In an embodiment, the power drawn by the heater can be used to detect gas flow using the heater power duty cycle instead of the drawn heater current.

In an embodiment, an alternative process of detecting gas flow can be used that requires only a single average of the drawn heater current. This alternative method uses the steps of first calibrating the apparatus 1 to determine a threshold above which no gas flow is provided, measuring the resistance of the heater, and subsequently using a look-up table to determine the voltage corresponding to the measured resistance of the heater wire.

In an embodiment, the apparatus 1 can be used to detect if there is no or low gas flow to start with, for example, by calibrating for the heater. Thus, once the apparatus 1 is warmed up, it can detect if there is no flow using a threshold or cut-off value.

Figure 10:
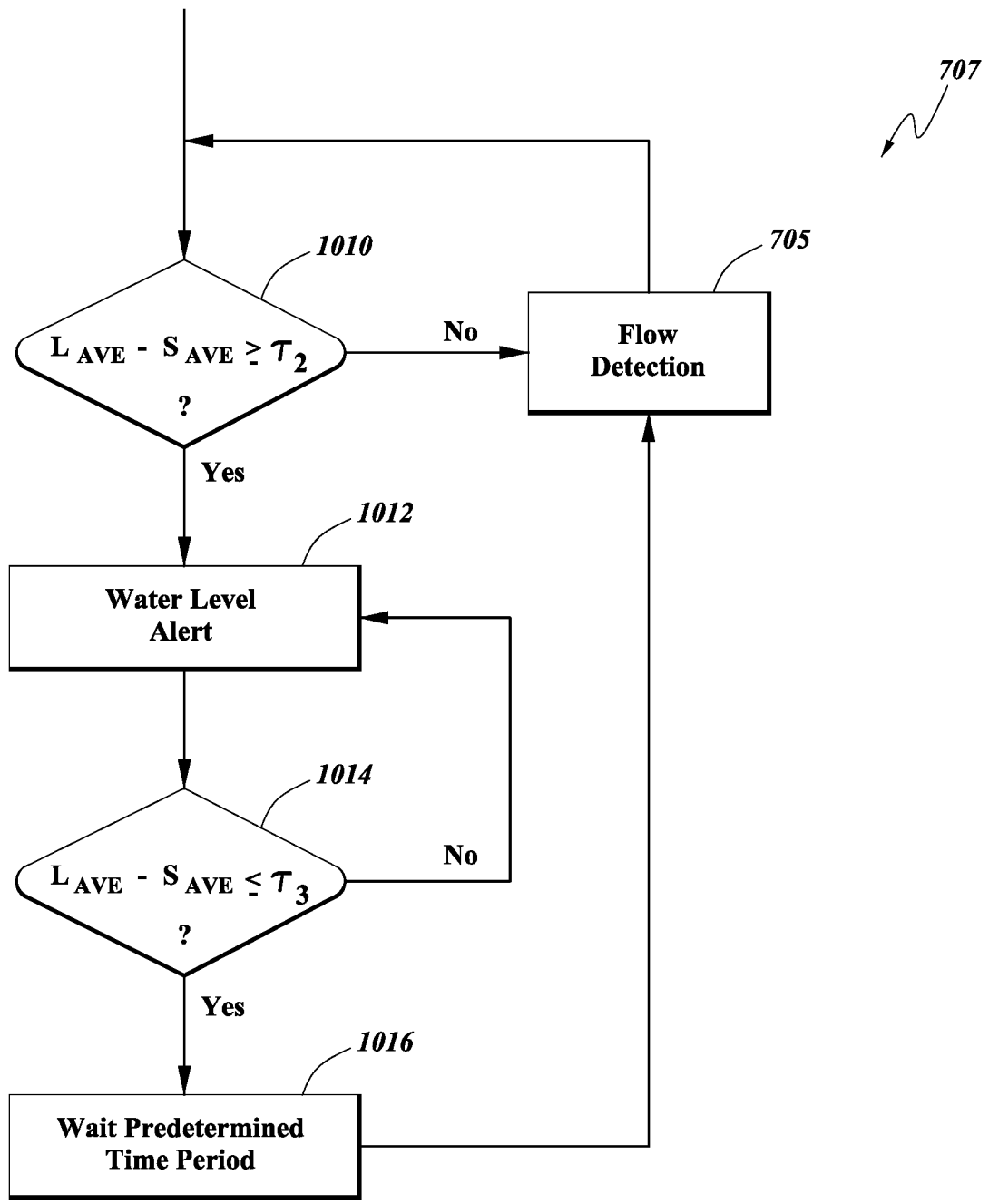

The liquid level detection process 707 helps to ensure that dry gas is not delivered to the patient. An embodiment of the process 707 operation is illustrated in FIG. 10.

The liquid level detection process 707 can be activated once the common initial warm-up procedure 701 is complete, or after the flow detection process 705 has determined that there is gas flow, or independently of either condition.

The liquid level detection process 707 determines if humidification liquid is present in the humidifier chamber by comparing the difference between the long term average $L_{AVE}$ and the short term average $S_{AVE}$ of an electrical characteristic of the heater, such as the heater power duty cycle. If, at step 1010, the difference between the long term average and the short term average is greater than or equal to a threshold value $\tau_2$, the liquid level detection process 707 determines that there is no humidification liquid, or only a low level of humidification liquid, in the chamber 5, and may activate a water-out indicator at step 1012. The statements above regarding the use of multiple types of difference comparisons apply here as well.

The liquid level detection process 707 can also be configured to determine, at step 1014, if the difference, again calculated as the long term average minus the short term average of the heater current, is less than a predetermined threshold $\tau_3$. If the difference is below the threshold, it is indicative that humidification liquid is present in the chamber 5. If it is determined that humidification liquid is present in the humidification chamber, further monitoring of the power duty cycle and/or drawn current of the heater can be delayed at step 1016 until a stabilization time period has elapsed. This allows the system to stabilize. The liquid level detection process 707 can therefore also detect if humidification liquid has been added using this method. As discussed above, other types of calculations can be performed using similar data and the presently described embodiment is not intended to be limiting.

Using long and short term averages of the heater power duty cycle and/or drawn heater current helps to minimize any variations that might occur under different environmental conditions. This can include, for example, the use of different types of humidification chambers or heater plates, power fluctuations, and/or changes in ambient temperatures. Using long and short term averages also allows for calibration of the system.

The controller 21 can be configured to detect if the chamber 5 is empty at the start of a medical procedure by having a predetermined profile of an electrical characteristic of the system relative to the level of humidification liquid in the chamber 5. The profile can be determined, for example, by experimentation or using pre-stored data. Thus the controller 21 can perform an initial monitoring step of monitoring an electrical characteristic of the system in use. The controller 21 can compare that monitoring of, for example, the drawn heater current in use with the predetermined profile of drawn heater current relative to the level of humidification liquid in the chamber 5 to determine whether or not the chamber 5 is empty. If the chamber 5 is empty, the heater temperature may overshoot or be unstable.

The controller 21 can further be configured to detect gas flow entering the apparatus, as excess humidity in the system may compromise optical clarity to a medical practitioner, as stated above. Thus, the controller may be arranged to control the generation of humidifying vapor initially, in dependence upon the flow of gas detected.

Liquid level detection can alternatively, or in addition, be performed using optical sensing, capacitance, or other methods.

Alternative embodiments may comprise any additional components as required.

The above processes have been described in relation to a medical gas delivery apparatus for use in a medical or surgical procedure, such as during open or closed surgery, or during a closed medical procedure such as endoscopy or laparoscopy. However, it will be appreciated that the described flow detection process 705 and liquid level detection process 707 can equally be used in any other type of gas delivery apparatus designed to deliver heated and/or humidified gas to a patient. For example, the system can alternatively comprise a respiratory assistance apparatus arranged to deliver breathing gas to a patient to assist with breathing.

Figure 11:
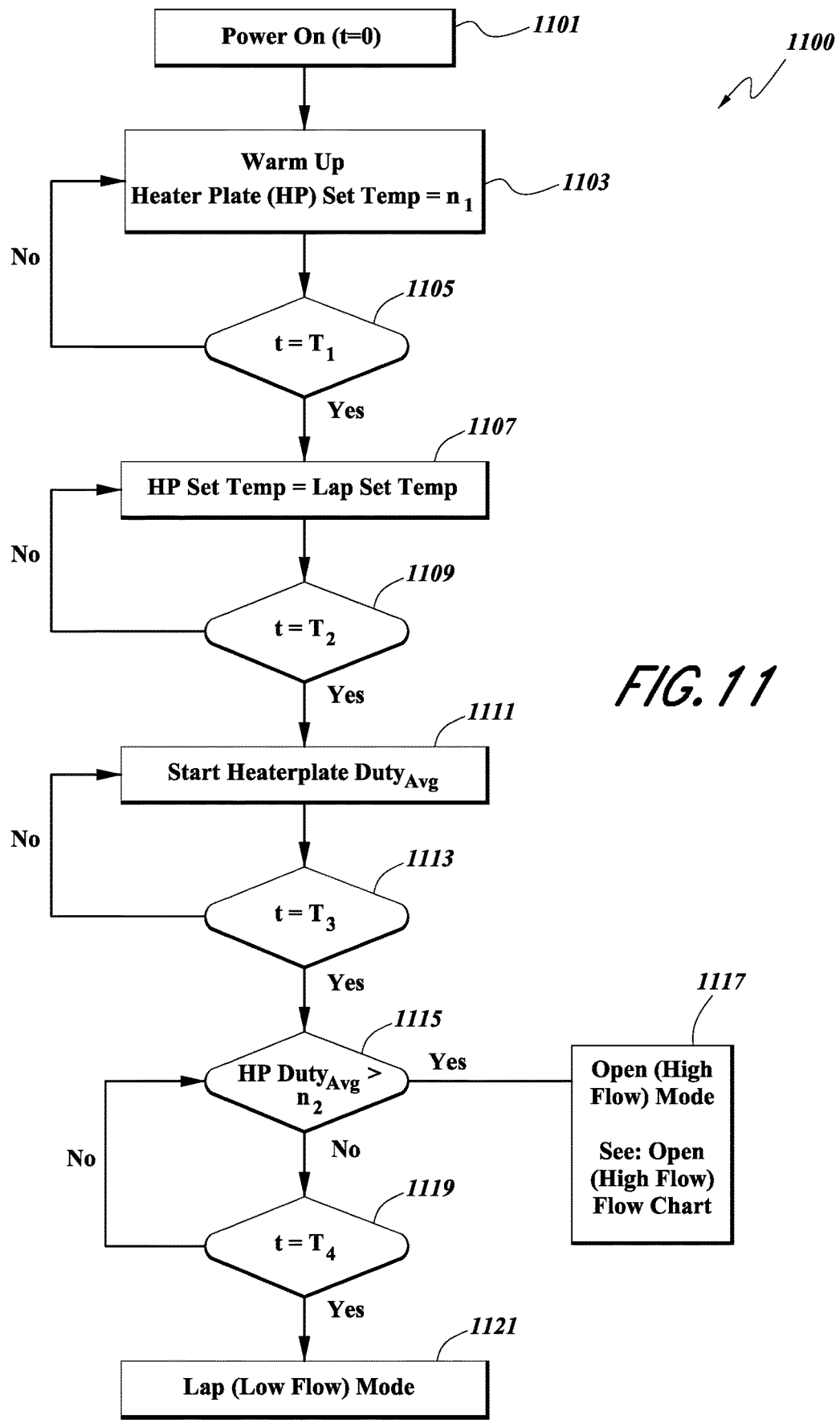
FIG. 11 is a flow diagram of an example embodiment of a method of determining whether the medical gas delivery system is being used for an open or closed type medical procedure.

FIG. 11 illustrates another embodiment of a process for determining whether an open (high flow) or closed (low flow) procedure is being performed with the gas supply device. The process 1100 starts at 1101 where the heater plate (HP) power is turned on at time zero (0). The heater plate is warmed up to a variable temperature set point $n_1$ at 1103 based on the amount of time that has passed since the warm-up process began. This gives the effect of warming the heater plate at a predetermined rate so that the system does not heat up too fast. As explained below, with respect to FIGS. 14-16, heating the system up too quickly results in increased condensation in the system. Thus, it is advantageous to provide a warm-up process that reduces condensation while achieving a desired temperature set point without undue delay. In an embodiment, the warm-up process continues for a predetermined period of time $T_1$ as checked at 1105. In an embodiment, the period of time $T_1$ is 15 minutes. The warm-up period can also be passed on the initial and ambient temperatures and/or humidity levels determined in the system.

Once the initial warm-up period is complete, the process then moves to 1107 and 1109 where the process checks to see if the heater plate temperature is equal to a predetermined laparoscopic set point temperature for a predetermined period of time $T_2$. In an embodiment, the predetermined period of time $T_2$ is 21 minutes. The process then moves to 1111 and 1113 where the process monitors the heater plate duty cycle averages. The heater plate average is determined over a third time period $T_3$. In an embodiment, $T_3$ is 25 minutes. The process then checks to see if the previously determined average heater plate duty cycle is greater than a predetermined duty cycle $n_2$ at 115. In an embodiment, $n_2$ is equal to 5. If the average duty cycle is not greater than $n_2$, then the system checks to see if it has already monitored the duty cycle for a period of time $T_4$ at 1119. If not, the process continues to monitor the average duty cycle. In an embodiment, $T_4$ is 37 minutes. If at 1119 the time is greater than $T_4$, then the process moves to 1121, where the process determines that the respiratory assistance system is in laparoscopic mode. If at 1115 the average duty cycle is greater than $n_2$, then the process moves to 1117 where the process determines the respiratory assistance system is in open (or high flow) mode. At this point the system moves on to the open mode process described in FIG. 12.

Figure 12:
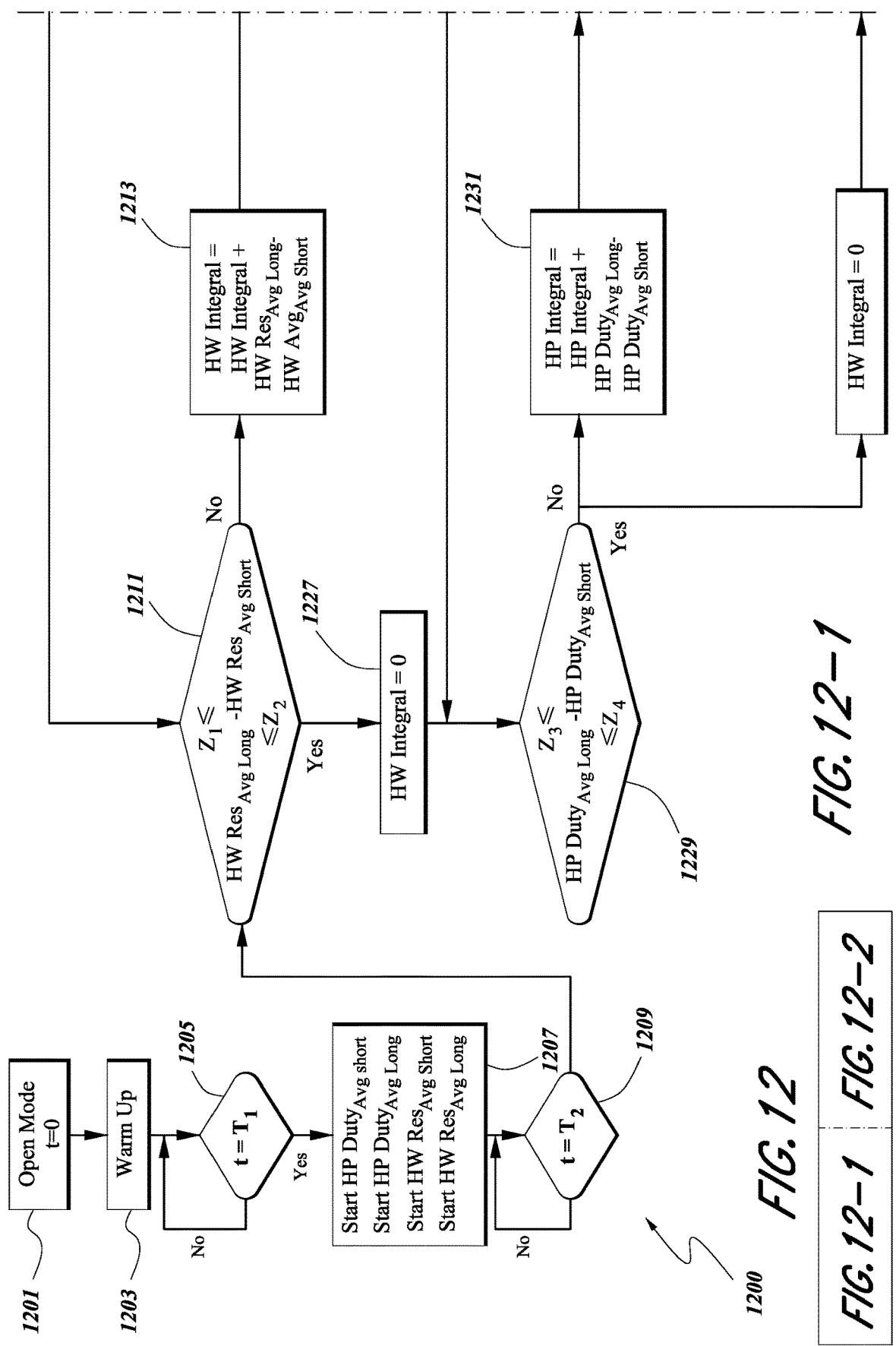
Figures 2, 12:
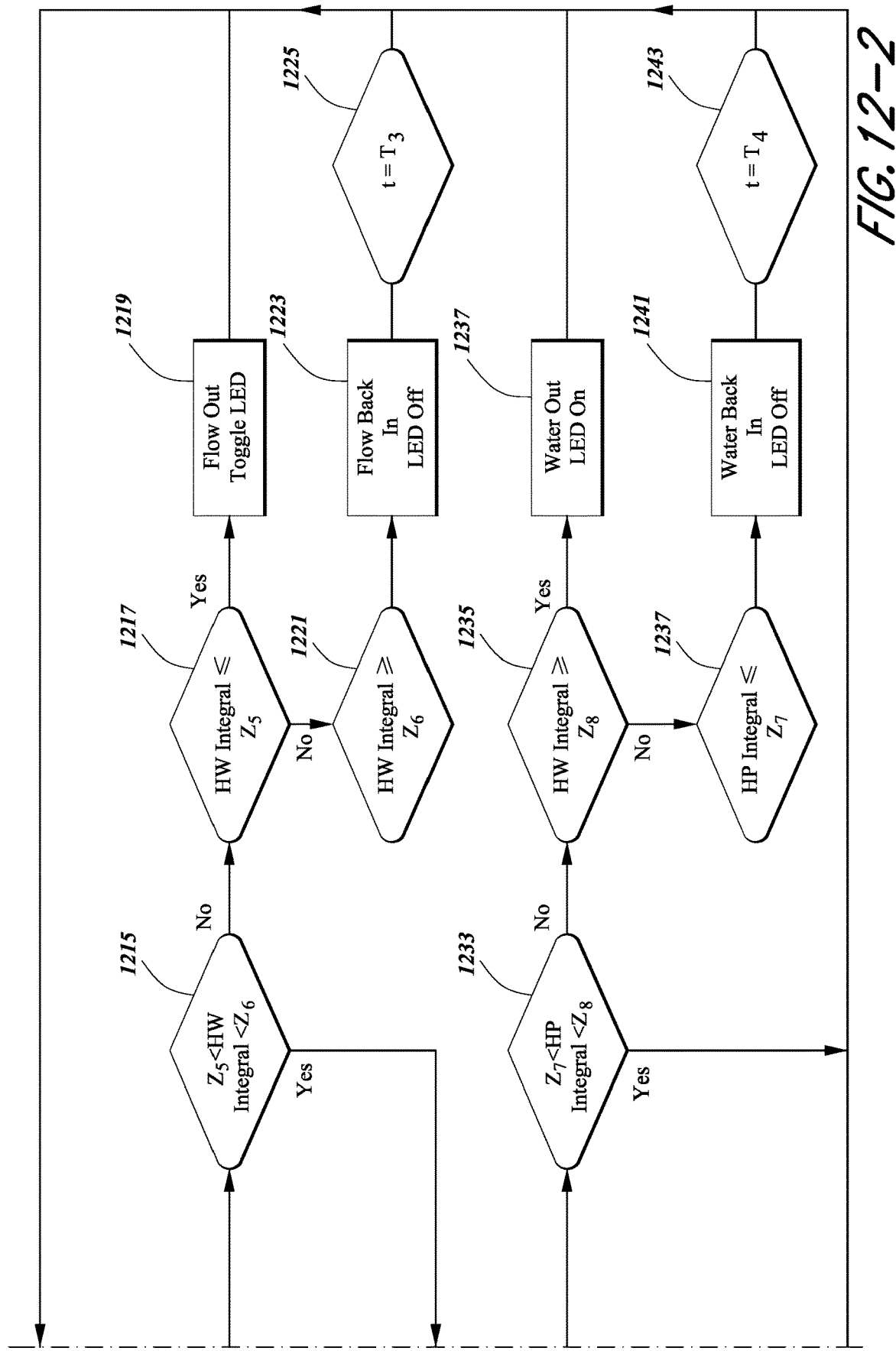

FIG. 12 illustrates an embodiment of an open (or high flow) process. This process recognizes that a history of certain electrical properties of the system are an important factor in determining the current state of the process and the respiratory assistance device. Thus, the open mode process of FIG. 12 includes the use of "Integrals" that are running summations of certain electrical properties over time that are kept under certain conditions.

For example, in FIG. 9 (and its associated description) in step 905, the difference between the long term average and the short term average of an electrical characteristic of the system, for example the drawn heater current, is used to determine a flow and/or water out condition or a flow and/or water in condition.

The open mode process of FIG. 12 comprises an alternative more robust comparison of differences over time between the long and short term averages using an Integral or running summation of the difference.

$$\text{Integral} = \text{Integral} + (L_{AVE} - S_{AVE}) \qquad \text{Eq. 1}$$

This more robust comparison can help to decrease random fluctuations that may occur in the system. This can be used for both water out detection and flow out detection. Equation 1, for example, is used in step 1231 shown in FIG. 12C. If $(L_{AVE} - S_{AVE})$ falls within the specified range then the Integral is set to zero. Once the Integral falls outside of a specific range, information can be given regarding a flow and/or water out condition or a flow and/or water in condition. The system may also be able to turn off the heater wire if no water is detected in the chamber to prevent hot dry gas from being delivered.

Another alternative formulation of a difference comparison utilizes both upper and lower bounds.

$$\text{IF:} ((L_{AVE} - S_{AVE}) < a) \& ((L_{AVE} - S_{AVE}) > b)$$

THEN: Integral=0

$$\text{ELSE: Integral} = \text{Integral} + (L_{AVE} - S_{AVE}) \qquad \text{Eq. 2}$$

The values of variables a and b are determined by experimentation. Once the Integral value reaches its set upper or lower bound, flow or water out/in detection has been determined.

With reference to the process described in FIG. 12 (separated into FIGS. 12-1 and 12-2), the process starts at 1201 once the respiratory assistance system is determined to be in open mode. At 1203, the process begins a separate open mode warm-up process. The warm-up process is continued until at 1205 it is determined that a predetermined warm-up period $T_1$ has passed. In an embodiment, $T_1$ is 5 minutes. The process then moves to 1207 where various electrical characteristics are monitored. These characteristics can include the characteristics described above with respect to FIGS. 7-9 and can also include the heater wire resistance. In the embodiment of FIG. 12, short and long term averages of the heater wire resistance are calculated in addition to short and long term averages of the heater plate duty cycle. These characteristics are monitored for a period of time $T_2$ at 1209. In some embodiments, $T_2$ is 10 minutes. The process then moves to 1211 where the difference in the long and short term heater wire resistances is analyzed to determine if it falls within a specified range, such as, for example, between −0.085 and 0.35. In an alternate embodiment, the specified range may be between −0.05 and 2.0. If the difference in the long and short term heater wire resistance averages falls within this range, then the process moves to 1227 where the heater wire Integral is sent to zero. If the difference in the long and short term heater wire resistance averages falls outside of the above described range, then the process moves to 1213 where the heater wire Integral is updated to be the previous (or initial) heater wire Integral plus the difference between the long and short term heater wire resistance averages. This process allows monitoring of the system over a period of time so that small blips or inconsistencies in the monitored data do not trigger an alarm event unnecessarily. After 1213, the process moves to 1215 where the updated heater wire Integral is analyzed to determine if it falls in a certain predefined range, such as, for example, between −500 and 200. If the updated heater wire Integral falls in this range, then the process moves to 1229 described below. If the heater wire Integral does not fall into this range, then if the heater wire Integral is less than a threshold, for example, −500 at 1217, then a flow out alert is activated at 1219 and the process returns to 1211. If the heater wire Integral is greater than a threshold, for example, 200 at 1221, then the process turns off the flow back in alert at 1223 and waits a predetermined time $T_3$, for example, 30 minutes, before returning to 1211.

Returning to the discussion of step 1227, once the heater wire Integral has been zeroed, the process moves onto step 1229 where the difference between the heater plate duty cycle long and short term averages is analyzed to determine if the averages fall into a predetermined range. This range, for example, is between −3.5 and 2.5. If the difference in the short and long term averages of the heater plate duty cycle do fall in this range, then the heater plate Integral set equal to zero at 1230 and the process returns to step 1211. If the difference in the short and long term averages of the heater plate duty cycle do not fall in the above range, then the process moves to 1231 where the heater plate Integral is updated to equal the current heater plate Integral value plus the difference in the short and long term heater plate duty cycle averages. The process then moves to 1233 where the updated heater plate Integral is analyzed to determine if it falls in a second range, for example, −200 and 1000. If the heater plate Integral does fall within this range, then the process returns to step 1211. If the heater plate Integral does not fall in this range at 1233, the process moves to step 1235 where if the heater plate Integral is greater than a predetermined threshold, for example, 1000, then the process determines the water is out and indicates an alert at 1237. The process then returns to step 1211. If the heater plate Integral is less than a threshold, for example, −200 at 1237, then the process determines at 1241 that water is back in and the water out alert is turned off. The system then waits a predetermined period of time $T_4$, for example, 30 minutes before returning to step 1211.

Figure 13:
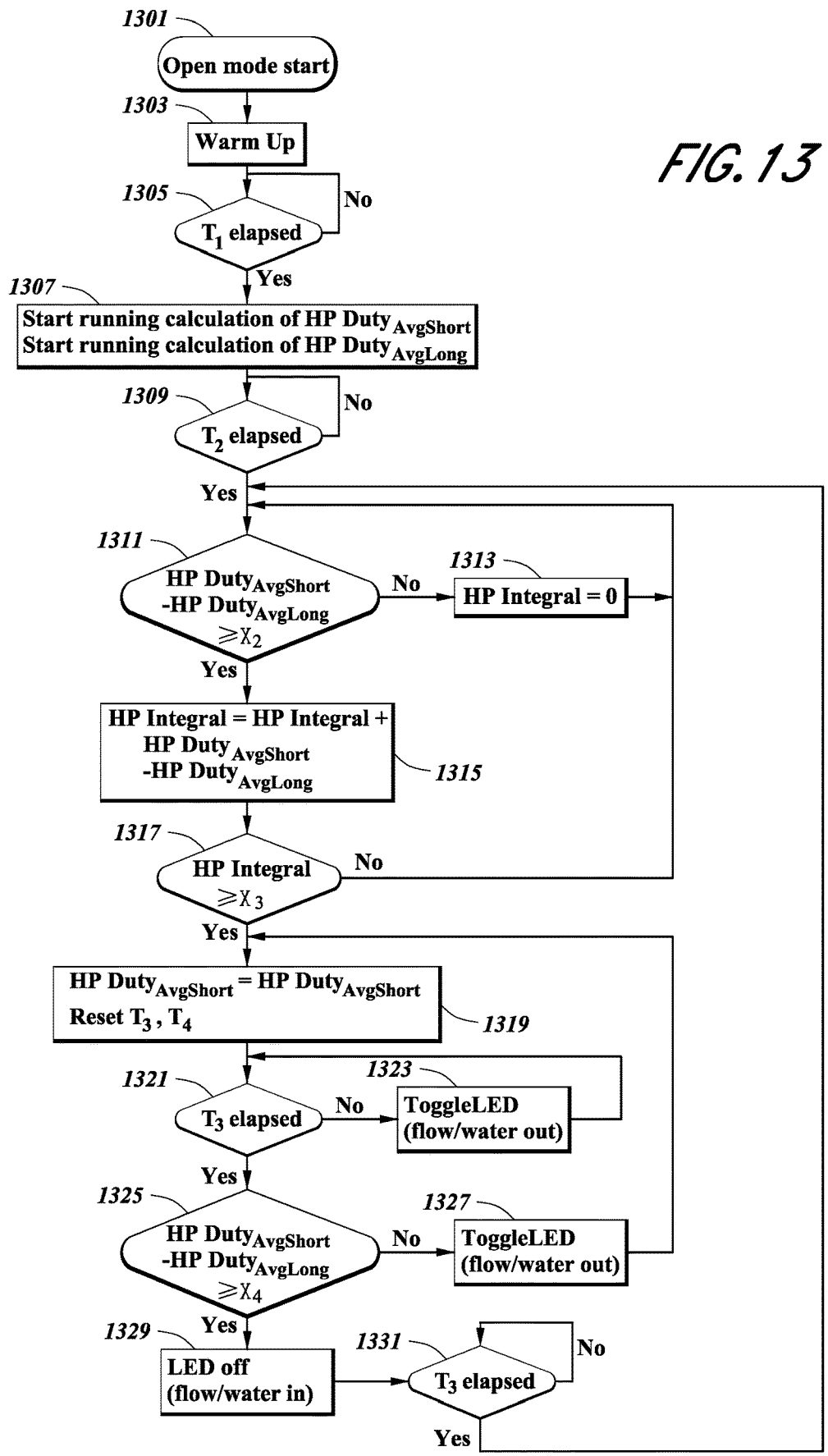
FIG. 13 is a flow diagram of an example embodiment of a method of controlling a medical gas delivery system in open mode.

FIG. 13 illustrates another embodiment of an open mode process that comprises a faster return of water determination. The process starts at 1301 once the respiratory assistance system is determined to be in an open mode. At 1303, the process begins a separate open mode warm-up process. The warm-up process is continued until at 1305 it is determined that a predetermined warm-up period $T_1$ has passed. In an embodiment, $T_1$ is 5 minutes. The process then moves to 1307 where various electrical characteristics are monitored. These characteristics can include, for example, a short term and a long term average of the heater plate duty cycle. Alternatively or in addition, any of the characteristics described above with respect to FIGS. 7-9. These characteristics are monitored for a period of time $T_2$ at 1309. In some embodiments, $T_2$ is 10 minutes. The process then moves to 1311 where the difference in the long and short term heater plate duty cycle is analyzed to determine if it falls within a specified range or is greater than a threshold. As shown in FIG. 13, if the long term average minus the short term average of the heater plate duty cycle is not greater than or equal to the specified threshold, $X_2$, then the process moves to step 1313 where the heater plate Integral is set equal to zero at 1313 and the process returns to step 1311. The threshold $X_2$ can be a nominal positive value selected to avoid hysteresis. Steps 1311 and 1313 can be considered normal operation where the power usage is relatively stable. If at 1311, the difference is greater than or equal to the specified threshold $X_2$, then the process moves to step 1315 where the heater plate Integral is updated to equal the current heater plate Integral value plus the difference between the long and short term heater plate duty cycle averages as shown in FIG. 13. The Integral represents an aggregate amount of the power usage and is analyzed at step 1317 to determine if the power usage has fallen by a certain aggregate amount. At 1317 the updated heater plate Integral is analyzed to determine if it falls in a second range. For example, if the Integral at 1317 is not greater than a threshold $X_3$, then the process returns to normal operation at 1311. If, at 1317, the Integral is greater than or equal to $X_3$, the process returns to step 1311. At step 1319, the process determines if an immediately previously calculated short term average heater plate duty cycle is about equal with a most recent heater plate duty cycle short term average. If it is then the system activates a water and/or flow out status indicator. This can be an LED that is toggled or lit up. The process then waits a period of time $T_3$ at 1321 while activating the indicator at 1323. Once the time $T_3$ has passed, the process moves to 1325 where the process continues to activate the water and/or flow out indicator until the process determines that water and/or flow have returned to the system. At 1325, the process determines a most recent short term average heater plate duty cycle and subtracts an immediately previous short term average duty cycle. If the result is greater than or equal to a threshold $X_4$, then the process determines that water and/or flow have not returned and continues to activate the indicator at 1327. If at 1325, the result is greater than or equal to the threshold $X_4$, then the process moves to 1329 where the system turns off the indicator because it has determined that water and/or flow have been added back in. The system then waits a period of time $T_4$ at 1331 in order to allow the system to stabilize before returning to normal operation mode at 1311.

As would be understood by a person of skill in the art, the time periods and thresholds in the above described embodiments can be chosen according to various criteria to provide a system that exhibits various advantages and disadvantages. For example, shorter wait periods and tighter thresholds can speed the various processes and systems up, but may sacrifice reliability. Accordingly, the above examples are provided by way of explanation and not limitation.

Figure 14:
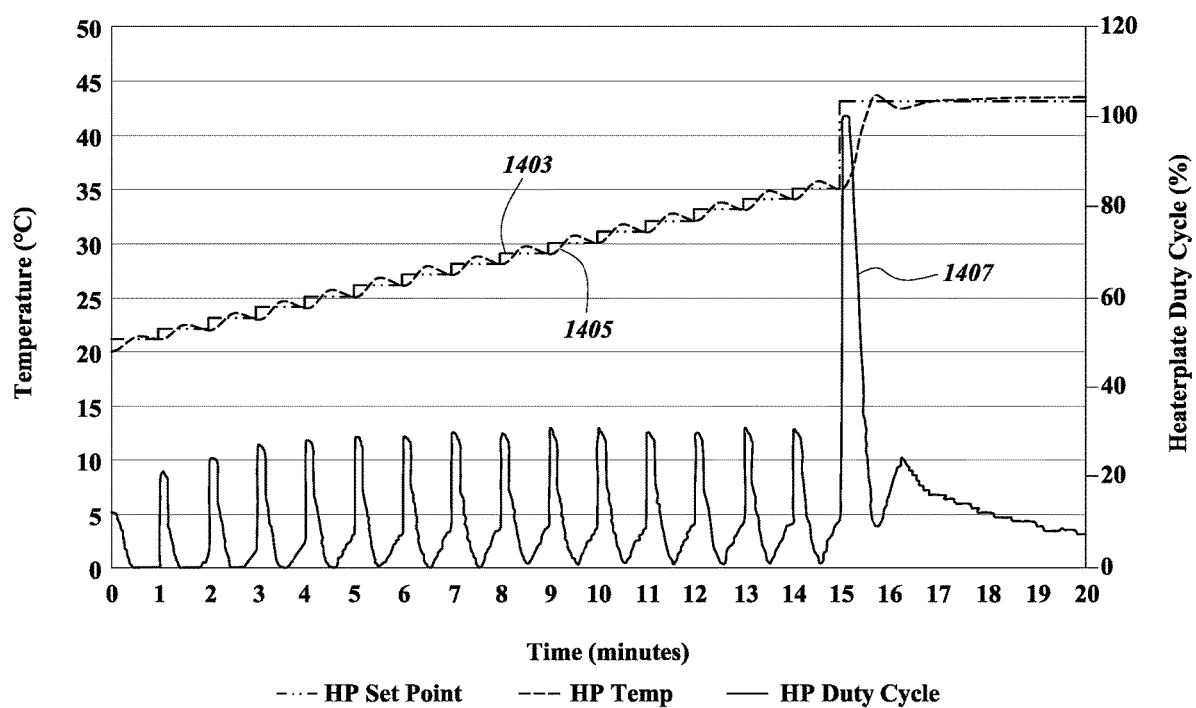
FIG. 14 is a chart illustrating example values of a heater plate set point temperature, a measured heater plate temperature, and a heater plate duty cycle during an embodiment of a warm-up period.

FIG. 14 is a graph demonstrating an embodiment of heater plate temperature control during the first period of operation as a means of providing controlled humidity delivery. This process can be implemented with respect to any and/or all of the warm-up processes described in the present disclosure. FIG. 14 illustrates the heater plate set point 1403, heater plate temperature 1405, and heater plate duty cycle 1407. This controlled humidity delivery process can be used to improve optical clarity for the surgeon. By controlling the level of humidity delivered, the colder surgical equipment has an opportunity to warm to the same temperature as the gas, lessening condensate formation on the equipment. In some embodiments, a linear equation can be used to adjust the set point temperature of the heater plate based on an initial set point temperature. The equation is:

$$\text{Set point temperature} = \text{gradient} * \text{time} + \text{initial set point temperature} \qquad \text{Eq. 3}$$

In the embodiment illustrated in FIG. 14, the initial set point temperature is 21° C. and the gradient is 1/60, such that for a time value measured in seconds, the set point temperature increases at a rate of 1° C. each minute.

If the starting heater plate temperature, that is, the heater plate temperature when the system is first switched on, is below the initial set point temperature, the system will supply power continuously to the heater plate to reach the initial set point temperature as quickly as possible, and then continue as defined by Equation 3. If the starting heater plate temperature is above the initial set point temperature, the system will not supply power to the heater plate until the set point temperature is equal to the heater plate temperature. This process is continued for a fixed amount of time, for example 15 minutes. For example, if the starting heater plate temperature is 30° C., the heater plate would not begin heating the liquid until time=9 minutes, but will then continue according to Equation 3. Depending on the starting heater plate temperature, the system will only start supplying power to the heater plate at the time and gradient dictated by Equation 3 in order for the heater plate temperature to reach the desired temperature by the end of the warm-up period.

After the specified warm-up period, the heater plate temperature will have reached a temperature that ensures the optimal humidity output for the type of procedure being performed. In an embodiment, the desired temperature is 43° C. for laparoscopic or 53° C. for open surgery.

Figure 15:
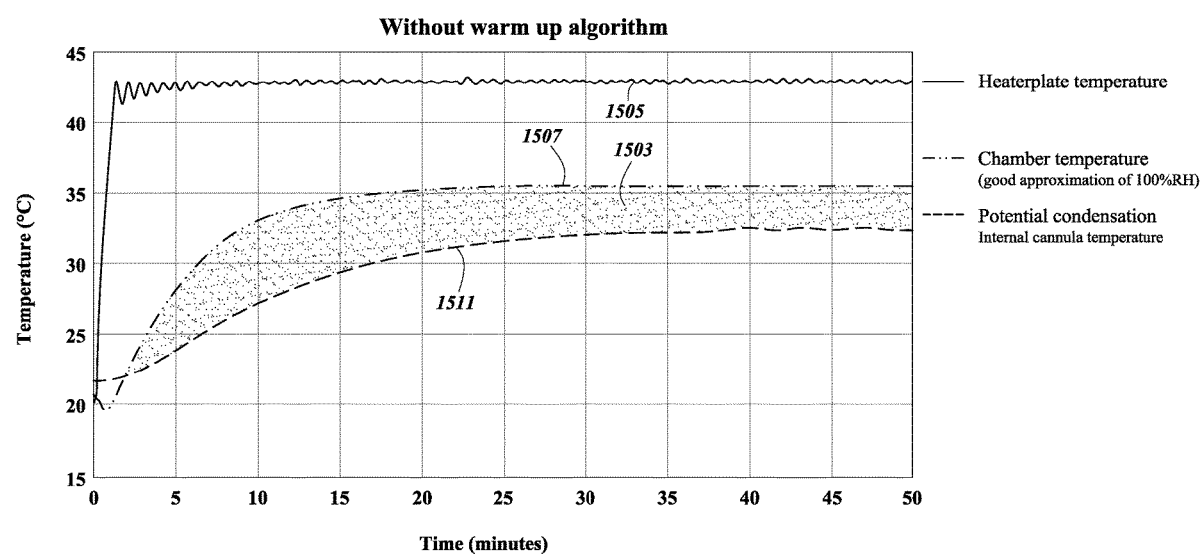
FIGS. 15-16 are charts illustrating a comparison of potential condensation during different embodiments of a warm-up period.
Figure 16:
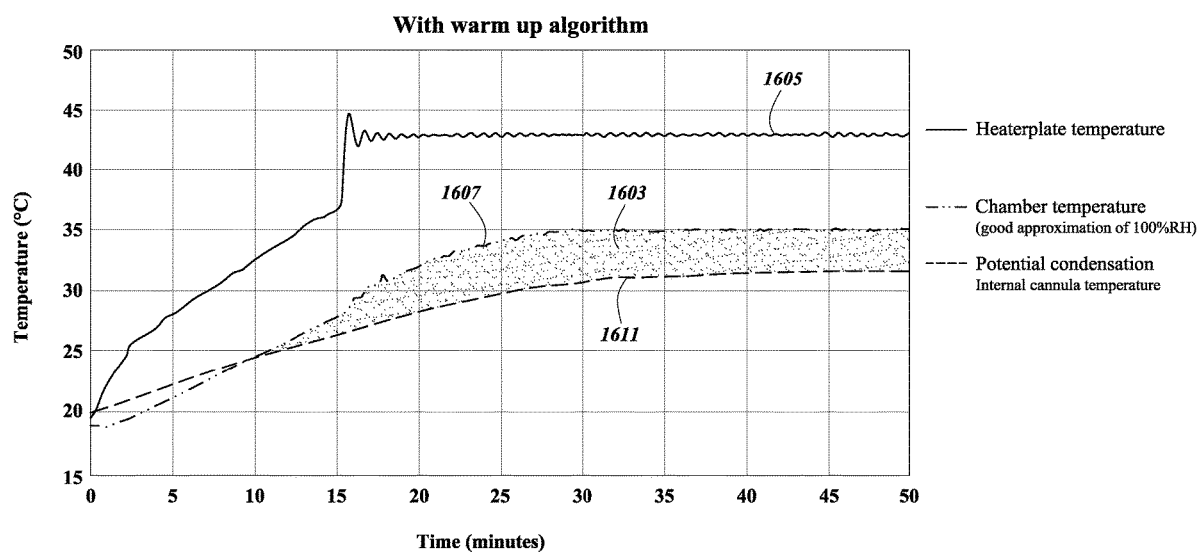

FIGS. 15 and 16 illustrate comparison examples of the reduction of condensation using the processes described in the present disclosure. FIG. 15 illustrates the condensation effect in a system where the warm-up process is not controlled, but rather the heater plate is warmed up as quickly as possible, as is typical for humidification systems in the prior art. As illustrated in FIG. 15, the heater plate temperate 1505 is quickly brought to its operating temperature of around 43° C. The water chamber temperature 1507 rises quickly with the heaterplate temperature, but the internal cannula temperature 1511 lags significantly behind the heaterplate and the chamber. Thus, the potential for condensation, illustrated as the differential area 1503 between the chamber temperature and cannula temperature is significant. FIG. 16 on the other hand illustrates the reduction in potential condensation using the warm-up procedure described in the present disclosure. FIG. 16 again illustrates the heater plate temperature 1605, but in this example, the heater plate temperature rise during the warm-up process is specifically controlled to rise at a slower rate before it reaches its operating temperature of around 43° C. This results in the chamber temperature also rising but in a controlled manner. As a result of this controlled warm-up process, the differential between the internal cannula temperature 1611 and the chamber temperature 1607 is much less during the warm-up period. This results in a lower potential for condensation 1603.

From the foregoing it will be seen that a medical gas delivery apparatus and method is provided that can, at least to some extent, control the mode of operation of the apparatus, activate an indicator of zero or reduced gas flow and/or an indicator of zero or low level of humidification liquid. This is done by analyzing the electrical characteristics of the humidifier heater and/or the delivery gas conduit heater, without requiring the use of external temperature or flow sensor probes. That is, the response, or change in response, exhibited by one or more of the heaters is used to determine the occurrence of particular events and/or to control the apparatus accordingly.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although the disclosed apparatus and methods have been described by way of example and with reference to possible embodiments thereof, it is to be understood that modifications or improvements may be made thereto without departing from the scope of the disclosure. The disclosed apparatus and methods may also be said broadly to consist in the parts, elements and features referred to or indicated in the specification of the application, individually or collectively, in any or all combinations of two or more of said parts, elements or features. Furthermore, where reference has been made to specific components or integers of the disclosed apparatus and methods having known equivalents, then such equivalents are herein incorporated as if individually set forth.

Any discussion of the prior art throughout the specification should in no way be considered as an admission that such prior art is widely known or forms part of common general knowledge in the field.

What is claimed is:

1. A system that controls gas delivery to a patient during a medical procedure, the system comprising:
   a heater arranged to heat at least one of a gas or a humidification liquid; and
   a hardware controller, the hardware controller configured to monitor an electrical characteristic of the heater;
   wherein the hardware controller is configured to automatically select a mode of operation from a plurality of modes of operation based, at least in part, on the monitored electrical characteristic of the heater without using input from sensors that are in direct contact with the gas including flow, pressure or temperature sensors, wherein the plurality of modes of operation include at least a first mode and a second mode, and wherein the first and second modes relate to open and closed medical procedures.

2. The system of claim 1, wherein the first mode relates to the open medical procedure using a first flow rate of gas.

3. The system of claim 2, wherein the first flow rate of gas is a relatively high flow rate of gas.

4. The system of claim 1, wherein the second mode relates to the closed medical procedure using a second flow rate of gas.

5. The system of claim 4, wherein the second flow rate of gas is an intermittent or a relatively low flow rate of gas.

6. The system of claim 4, wherein the closed medical procedure is laparoscopic surgery.

7. The system of claim 1, wherein the monitored electrical characteristic is power drawn by the heater.

8. The system of claim 7, wherein the monitored electrical characteristic is a power duty cycle of the heater.

9. The system of claim 1, wherein the hardware controller is further configured to monitor the electrical characteristic of the heater for a predetermined time period and calculate an average of the monitored electrical characteristic of the heater for that time period.

10. The system of claim 9, wherein the hardware controller is further configured to select the mode of operation in response to a comparison of the calculated average of the monitored electrical characteristic of the heater with a predetermined threshold.

11. The system of claim 1, wherein the hardware controller is further configured to execute an initial heater warm-up process where the heater is allowed to warm up.

12. The system of claim 11, wherein the hardware controller is further configured to switch on the heater and allow the heater to warm up prior to the monitoring of the electrical characteristic of the heater.

13. A method of controlling a system arranged to deliver gas to a patient during a medical procedure, the method comprising:
   using a hardware controller:
      monitoring an electrical characteristic of a heater of the system, wherein the heater is configured to heat at least one of the gas or a humidification liquid; and
      automatically selecting a mode of operation from a plurality of modes of operation based, at least in part, on the monitored electrical characteristic of the heater without using input from sensors that are in direct contact with the gas including flow, pressure or temperature sensors wherein the plurality of modes of operation include at least a first mode and a second mode, and wherein the first and second modes relate to open and closed medical procedures.

14. The method of claim 13, wherein the first mode is associated with an open medical procedure using a first flow rate of gas.

15. The method of claim 14, wherein the first flow rate of gas is a relatively high flow rate of gas.

16. The method of claim 13, wherein the second mode is associated with a closed medical procedure using a second flow rate of gas.

17. The method of claim 16, wherein the second flow rate of gas is an intermittent or a relatively low flow rate of gas.

18. The method of claim 16, wherein the closed surgery is laparoscopic surgery.

19. The method of claim 13, wherein the monitored electrical characteristic is power drawn by the heater.

20. The method of claim 13, wherein the monitored electrical characteristic is a power duty cycle of the heater.

21. The method of claim 13, wherein the electrical characteristic is monitored for a first predetermined period of time, and wherein the method further comprises calculating a first average of the electrical characteristic over the first predetermined period of time, and comparing the first calculated average of the monitored electrical characteristic with a predetermined threshold.

22. The method of claim 21 further comprising selecting the first mode of operation if the first calculated average is above the predetermined threshold.

23. The method of claim 21 further comprising:
   if the first calculated average is equal to or below the predetermined threshold,
   monitoring the electrical characteristic of the heater for a second predetermined period of time, calculating a second average of the monitored electrical characteristic over the second time period, and comparing the second calculated average of the monitored electrical characteristic to the predetermined threshold.

24. The method of claim 23 further comprising selecting the first mode of operation if the second calculated average is above the predetermined threshold.

25. The method of claim 23 further comprising selecting the second mode of operation if the second calculated average is equal to or below the predetermined threshold.

* * * * *